(12) United States Patent
Carlucci et al.

(10) Patent No.: US 6,413,247 B1
(45) Date of Patent: Jul. 2, 2002

(54) ABSORBENT ARTICLE WITH BREATHABLE DUAL LAYER BACKSHEET COMPRISING ONE LAYER WITH SLANTED CAPILLARY APERTURES

(75) Inventors: Giovanni Carlucci, Chieti; Carmine Cimini, Pescara; Amedeo Franco D'Incecco, Pescara; Luigi Marinelli, Pescara; Paolo Veglio, Pescara, all of (IT)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 09/601,592

(22) PCT Filed: Feb. 3, 1999

(86) PCT No.: PCT/US99/02393

§ 371 (c)(1),
(2), (4) Date: Aug. 4, 2000

(87) PCT Pub. No.: WO99/39673

PCT Pub. Date: Aug. 12, 1999

(51) Int. Cl.[7] .......................... A61F 13/15; A61F 13/20
(52) U.S. Cl. .......... 604/385.01; 604/384; 604/385.101; 604/358; 428/132
(58) Field of Search .............................. 604/378, 384, 604/385.101, 358

(56) References Cited

U.S. PATENT DOCUMENTS

| 3,881,489 A | 5/1975 | Hartwell |
| 3,989,867 A | 11/1976 | Sisson |
| 5,591,510 A | 1/1997 | Junker et al. |

FOREIGN PATENT DOCUMENTS

| EP | 0 304 617 A2 | 3/1989 |
| WO | WO 97/24096 | 7/1997 |
| WO | WO 97/26850 | 7/1997 |

*Primary Examiner*—A. Vanatta
*Assistant Examiner*—Angela J Grayson
(74) *Attorney, Agent, or Firm*—Matthew P. Fitzpatrick; Ingrid N. Hickman; Kevin C. Johnson

(57) ABSTRACT

A breathable disposable absorbent articles of layered construction, each layer having a garment facing surface, and a wearer facing surface. The breathable disposable absorbent article comprises at least a first backsheet layer and a second backsheet layer. At least one of the breathable layers of the backsheet comprises a resilient, three-dimensional web, which consists of a liquid impervious polymeric film having apertures. The apertures form capillaries, which are not perpendicular to the plane of the film but are disposed at an angle of less than 90° measured from the plane of the film.

11 Claims, 4 Drawing Sheets

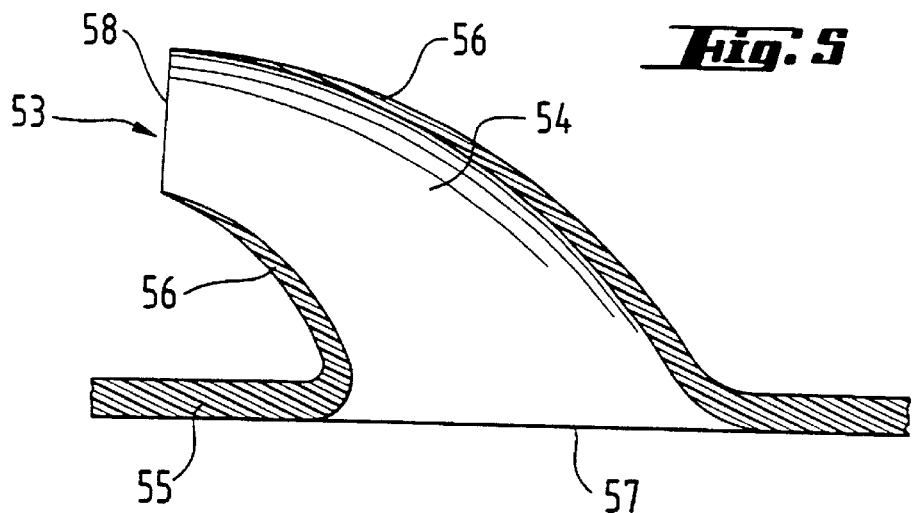
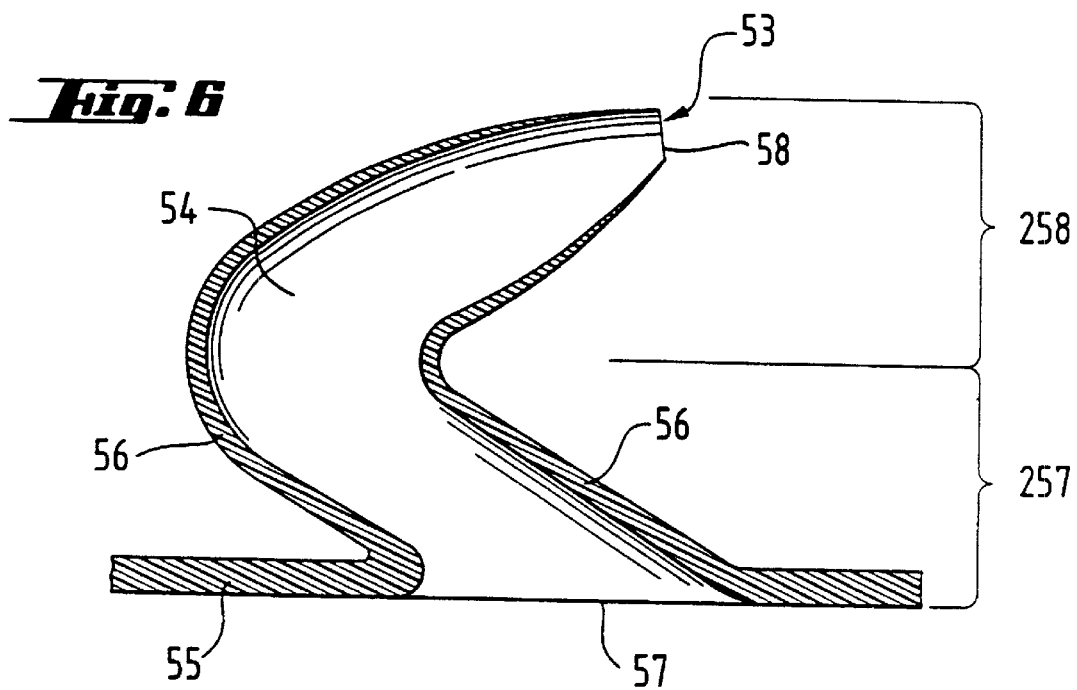

ABSORBENT ARTICLE WITH BREATHABLE DUAL LAYER BACKSHEET COMPRISING ONE LAYER WITH SLANTED CAPILLARY APERTURES

FIELD OF THE INVENTION

The present invention relates to breathable absorbent articles like baby diapers, adult incontinence articles and in particular to sanitary napkins or pantiliners. According to the present invention the articles are provided with an apertured backsheet for breathability. At least one of the breathable layers of the backsheet comprises a resilient, three dimensional web which consists of a liquid impervious polymeric film having apertures. The apertures form capillaries which are not perpendicular to the plane of the film but are disposed at a angle of less than 90° relative to the plane of the film.

BACKGROUND OF THE INVENTION

The primary consumer needs which underlie development in the absorbent article field, in particular sanitary napkins, catamenials, or pantiliners is the provision of products providing both a high protection and comfort level.

One means for providing consumer comfort benefits in absorbent articles is by the provision of breathable products. Breathability has typically concentrated on the incorporation of so called 'breathable backsheets' in the absorbent articles. Conmmonly utilised breathable backsheets are microporous films and apertured formed films having directional fluid transfer as disclosed in for example U.S. Pat. No. 4,591,523. Both these types of breathable backsheets are vapour permeable allowing gaseous exchange with the environment. This thereby allows for the evaporation of a portion of the fluid stored in the core and increases the circulation of air within the absorbent article. The latter is particularly beneficial as it reduces the sticky feeling experienced by many wearers during use, commonly associated with the presence of an apertured formed film or film like topsheet.

A drawback associated with the use of breathable backsheets in absorbent articles is the negative effect on the protection level performance by leakage, known as wet through, onto the users garment. Although, breathable backsheets in principle only allow the transfer of materials in the gaseous state, physical mechanisms such as extrusion, diffusion and capillary action may still occur and result in the transfer of the fluids from the absorbent core through the backsheet and onto the users garments. In particular, these mechanisms become more dominant if the product is utilised during physical exertion, or for heavy discharge loads or over extended periods of time. Thus, whilst the incorporation of breathable backsheets in absorbent articles is highly desirable from a comfort standpoint, since the primary role of a backsheet still remains the prevention of liquid leakage, conventional breathable backsheets have not been satisfactorily incorporated into products.

The problem of wet through onto users garments due to the incorporation of such breathable backsheets in absorbent articles has indeed also been recognized in the art. Attempts to solve the problem have mainly resided in the use of multiple layer backsheets such as those illustrated in U.S. Pat. No. 4,341,216. Similarly European patent application no. 710 471 discloses a breathable backsheet comprising an outer layer of a gas permeable, hydrophobic, polymeric fibrous fabric and an inner layer comprising an apertured formed film having directional fluid transport. The backsheet construction preferably has no liquid transport/wet through under certain specified test conditions. Also European patent application no. 710 472 discloses a breathable backsheet consisting of at least two breathable layers which are unattached to one another over the core area. The backsheet construction preferably has no liquid transport/ wet through under certain specified test conditions.

U.S. Pat. No. 4,713,068 discloses a breathable clothlike barrier for use as an outer cover for absorbent articles. The barrier comprises at least 2 layers, a first layer having a specified basis weight, fiber diameter and pore size and a second layer comprising a continuous film of poly (vinyl alcohol) having a specified thickness. The barrier also has a specified water vapour transmission rate and level of impermeability.

However, none of the above proposed solutions have been able to provide a fully satisfactory solution to the problem of breathable backsheet wet through under all conditions.

U.S. Pat. No. 5,591,510 as well as WO 97/03118 and WO 97/03795 disclose an apertured film layer having capillaries which are disposed at an angle relative to the plain of the film, which films are referred to as slanted capillary films. This film structure is provided as a improvement for incorporation into clothing and garments which are breathable, yet non transmitting liquids toward the wearer of such garments. Also the use of such slanted capillary films is indicated in the context of absorbent articles but as a topsheet, particularly in FIG. 16 of U.S. 5,591,510 the combination of such slanted capillary films together with an absorbent material is disclosed, however not in the context of disposable absorbent articles according to the present invention.

It is therefore an objective of the present invention to provide a disposable absorbent article having improved comfort while maintaining an acceptable level of protection, i.e. being exceptionally leakage resistant.

SUMMARY OF THE INVENTION

The present invention relates to breathable disposable absorbent articles of a layered construction such as baby diapers, adult incontinence articles and in particular sanitary napkins or panty liners. Also articles such as underarm sweat pads or shirt scholars may benefit from the present invention. Typically such articles are of layered construction with each layer or group of layers having a garment facing surface which is oriented to face in the direction of a garment during use of the article and a wearer facing surface facing in the opposite direction. Typically such articles comprise a liquid pervious topsheet forming the wearer facing surface of the article, an absorbent core and a breathable backsheet forming the garment facing surface of the article. The absorbent core is interposed between the topsheet and the backsheet. However, according to the present invention the absorbent core may provide the wearer facing surface of the article such that this surface of the core also provides the functions of the topsheet.

The breathable backsheet is located on the garment facing surface of the absorbent core and comprises at least a first backsheet layer and a second backsheet layer. The first backsheet layer is positioned between the garment facing surface of the absorbent core and the wearer facing surface of the second backsheet layer. In order to provide the article with breathability all backsheet layers are at least water vapor permeable, preferably air permeable. The first backsheet layer comprises a resilient three dimensional web, which consists of a liquid impervious polymeric film which film has apertures. The apertures form capillaries which have side walls which extend away from the wearer facing surface of the film providing the web with three dimensionality. The capillaries have a first opening in the garment facing surface of the film and a second opening at the end of the capillaries spaced apart from the wearer facing surface of the film. Importantly the capillaries extend away from the wearer facing surface of the film at an angle which is less than 90° in respect to the plain of the film.

In a preferred embodiment the capillaries are all substantially identical and preferably are homogeneously distributed across the film. Preferably a center axis of each capillary forms an angle between 85° and 20°, more preferably between 65° and 25° and most preferably between 55° and 30° with the plain of the film. The center axis is defined as the line which connects the center point of the first opening of a capillary and the center point of the second opening of a capillary.

For some embodiments it is also possible that the first opening of at least some of the capillaries is larger than the second opening of the respective capillary such that the capillaries themselves form cones which have an increase in capillary action in a direction towards the absorbent core. In yet another embodiment according to the present invention the capillaries are curved towards or appear bent towards the plain of the film. In an alternative or in addition thereto the capillaries have a first and a second portion which are different in direction, form, shape, size or combinations thereof.

Also the second opening of at least some of the capillaries may be provided as slits. Slits are considered to be such forms in which the longest extend of an opening is at least 5 times the length of the smallest length of the opening.

In general the construction of the absorbent article can be such that the web comprising the film forms the wearer facing surface of the backsheet construction. In this way the directional liquid transport and the ability to close under pressure derivable from the angled capillaries provide the best leak through protection while maintaining optimum breathability for improved comfort.

BRIEF DESCRIPTION OF THE DRAWINGS

FIGS. 2–7 show particular alternative embodiments of the slanted capillaries used for the three dimensional web comprised in the breathable backsheet according to the present invention.

DETAILED DESCRIPTION OF THE INVENTION

Figure 1:
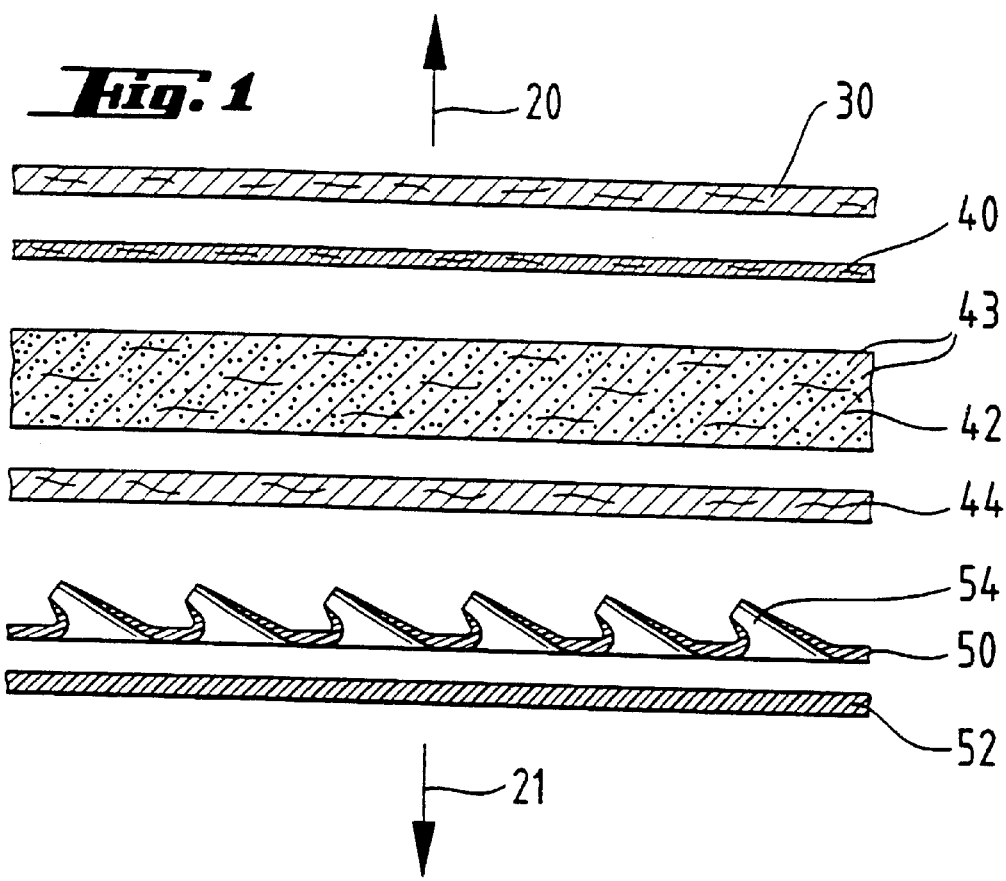
FIG. 1 shows a cross-sectional view of an absorbent article comprising all usual elements of such articles including an embodiment of the breathable backsheet according to the present invention.

The present invention relates to absorbent disposable articles such as sanitary napkins, panty liners, incontinence products sweatpads and baby diapers. Typically such products comprise the elements of a liquid pervious topsheet, a backsheet and an absorbent core intermediate said topsheet and said backsheet. According to the present invention the topsheet, backsheet and core may be selected from any of the known types of these components provided that they meet the desired comfort and protection performance requirements and conditions noted below and in the apended claims.

In general, the topsheet—if present—should have good liquid retention to maintain a dry surface and thereby keep the skin of the wearer dry; the absorbent core needs to provide enough absorbent capacity and allow the flow of vapour and/or air through it and the backsheet should prevent wet through (liquid permeability) to retain the absorbed fluid while being sufficiently breathable. Furthermore, the individual elements are joined, preferably using techniques such that the final product has the desired comfort and performance level.

In the following description of the invention the surface facing in the direction of the wearer is called wearer facing surface. In the drawings this direction is indicated by arrow 20. Further the surface facing in the direction of the garment is called garment facing surface and in the drawings this direction is indicated by arrow 21.

Absorbent Article Components

The Topsheet

According to the present invention the absorbent article usually comprises a topsheet. The topsheets suitable for use herein may be any topsheet known in the art. In FIG. 1 the topsheet is indicated with reference numeral 30.

The topsheets for use herein may comprise a single layer or a multiplicity of layers. In a preferred embodiment the topsheet comprises a first layer which provides the user facing surface of the topsheet and a second layer between the first layer and the absorbent structure/core. In addition another layer on the wearer facing surface of the first layer but only extending in the central zone or in parts of the peripheral zone of the article can be desirable to provide extra softness or extra liquid handling/retaining abilities (this design is usually referred to as "hybrid topsheet"). The topsheet typically extends across the whole of the absorbent structure and can extend into and form part of or all of the preferred sideflaps, side wrapping elements or wings.

The topsheet as a whole and hence each layer individually needs to be compliant, soft feeling, and non-irritating to the wearer's skin. It also can have elastic characteristics allowing it to be stretched in one or two directions. As used herein the topsheet hence refers to any layer or combination of layers whose principle function is the acquisition and transport of fluid from the wearer towards the absorbent core and containment of the absorbent core. In addition the topsheet of the present invention should have a high vapour permeability preferably also a high air permeability.

According to the present invention the topsheet may be formed from any of the materials available for this purpose and known in the art, such as wovens, non wovens, films or combinations thereof. In a preferred embodiment of the present invention at least one of the layers of the topsheet comprises a liquid permeable apertured polymeric film. Preferably, the wearer facing and contacting layer is provided by a film material having apertures which are provided to facilitate liquid transport from the wearer facing surface towards the absorbent structure, as detailed for example in U.S. Pat. Nos. 3,929,135, 4,151,240, 4,319,868, 4,324,426, 4,343,314 and 4,591,523. However, even non-woven or woven substrates can be apertured to improve their function of liquid acquisition.

Absorbent Core

According to the present invention the absorbent cores suitable for use herein may be selected from any of the absorbent cores or core system known in the art. As used herein the term absorbent core refers to any material or multiple material layers whose primary function is to absorb, store and distribute fluid. In FIG. 1 the absorbent structure is shown to comprise 3 layers 40, 42, and 44.

The absorbent core of the present invention should have a high vapour permeability preferably also a high air permeability. The absorbent core preferably has a caliper or thickness of less than 12 mm, preferably less than 8 mm, more preferably less than 5 mm, most preferably from 4 mm to 2 mm.

According to the present invention, the absorbent core can include the following components: (a) an optional primary fluid distribution layer preferably together with a secondary optional fluid distribution layer; (b) a fluid storage layer; (c) an optional fibrous ("dusting") layer underlying the storage layer; and (d) other optional components.

Primary/Secondary Fluid Distribution Layer

One optional component of the absorbent core according to the present invention, indicated as layer 40 in FIG. 1, is a primary fluid distribution layer and a secondary fluid distribution layer. The primary distribution layer typically underlies the topsheet and is in fluid communication therewith. The topsheet transfers the acquired fluid to this primary distribution layer for ultimate distribution to the storage layer. This transfer of fluid through the primary distribution layer occurs not only in the thickness, but also along the length and width directions of the absorbent product. The also optional but preferred secondary distribution layer typically underlies the primary distribution layer and is in fluid communication therewith. The purpose of this secondary distribution layer is to readily acquire fluid from the primary distribution layer and transfer it rapidly to the underlying storage layer. This helps the fluid capacity of the underlying storage layer to be fully utilised. The fluid distribution layers can be comprised of any material typical for such distribution layers.

b Fluid Storage Layer

Positioned in fluid communication with, and typically underlying the primary or secondary distribution layers, is a fluid storage layer (42). The fluid storage layer can comprise any usual absorbent material or combinations thereof. It preferably comprises absorbent gelling materials usually referred to as "hydrogel", "superabsorbent", hydrocolloid" materials in combination with suitable carriers, which are indicated as particles (43) in FIG. 1.

The absorbent gelling materials are capable of absorbing large quantities of aqueous body fluids, and are further capable of retaining such absorbed fluids under moderate pressures. The absorbent gelling materials can be dispersed homogeneously or non-homogeneously in a suitable carrier. The suitable carriers, provided they are absorbent as such, can also be used alone.

Suitable absorbent gelling materials for use herein will most often comprise particles of a substantially water-insoluble, slightly cross-linked, partially neutralised, polymeric gelling material. This material forms a hydrogel upon contact with water Such polymer materials can be prepared from polymerizable, unsaturated, acid-containing monomers which are well known in the art.

Suitable carriers include materials which are conventionally utilised in absorbent structures such as natural, modified or synthetic fibers, particularly modified or non-modified cellulose fibers, in the form of fluff and/or tissues. Suitable carriers can be used together with the absorbent gelling material, however, they can also be used alone or in combinations. Most preferred are tissue or tissue laminates in the context of sanitary napkins and panty liners.

An embodiment of the absorbent structure made according to the present invention comprises a double layer tissue laminate. These layers can be joined to each other for example by adhesive or melting a polymeric powder binder (e.g. PE powder), by mechanical interlocking, or by hydrogen bridge bends. Absorbent gelling material or other optional material can be comprised between the layers.

Modified cellulose fibers such as the stiffened cellulose fibers can also be used. Synthetic fibers can also be used and include those made of cellulose acetate, polyvinyl fluoride, polyvinylidene chloride, acrylics (such as Orlon), polyvinyl acetate, non-soluble polyvinyl alcohol, polyethylene, polypropylene, polyamides (such as nylon), polyesters, bicomponent fibers, tricomponent fibers, mixtures thereof and the like. Preferably, the fiber surfaces are hydrophilic or are treated to be hydrophilic. The storage layer can also include filler materials, such as Perlite, diatomaceous earth, Vermiculite, etc., to improve liquid retention.

If the absorbent gelling material is dispersed non-homogeneously in a carrier, the storage layer can nevertheless be locally homogenous, i.e. have a distribution gradient in one or several directions within the dimensions of the storage layer. Non-homogeneous distribution can also refer to laminates of carriers enclosing absorbent gelling materials partially or fully.

An alternative are foam like or actual foam structures as liquid storage. There are open cell foams which absorb liquid and through chemical or surface interaction retain the liquid also under pressure. Such foams may be formed with a skin, thus providing on their wearer facing surface a smooth appearance which makes the use of a topsheet optional. Typical foams in this context are e. g. those disclosed in PCT publications WO 93/03699, WO 93/04092, WO 93/04113.

c Optional Fibrous ("Dusting") Layer

An optional component for inclusion in the absorbent core according to the present invention is a fibrous layer adjacent to, and typically underlying the storage layer identified by reference numeral 44 in FIG. 1. This underlying fibrous layer is typically referred to as a "dusting" layer since it provides a substrate on which to deposit absorbent gelling material in the storage layer during manufacture of the absorbent core. Indeed, in those instances where the absorbent gelling material is in the form of macro structures such as fibers, sheets or strips, this fibrous "dusting" layer need not be included. However, this "dusting" layer provides some additional fluid-handling capabilities such as rapid wicking of fluid along the length of the pad.

d Other Optional Components of the Absorbent Structure

The absorbent core according to the present invention can include other optional components normally present in absorbent webs. For example, a reinforcing scrim can be positioned within the respective layers, or between the respective layers, of the absorbent core. Such reinforcing scrims should be of such configuration as to not form interfacial barriers to fluid transfer. Given the structural integrity that usually occurs as a result of thermal bonding, reinforcing scrims are usually not required for thermally bonded absorbent structures.

Another component which can be included in the absorbent core according to the invention, and preferably is provided close to or as part of the primary or secondary fluid distribution layer or the fluid storage layer, are odor control agents such as zeolites, carbon black, silicates, EDTA or other chelates. Such agents are preferably provided in particulate form or as part of particles and can be provided together with the absorbent gelling material mentioned supra.

Backsheet

The absorbent article according to the present invention also comprises a breathable backsheet. The backsheet primarily has to prevent the extrudes absorbed and contained in the absorbent structure from wetting articles that contact the absorbent product such as underpants, pants, pyjamas, undergarments, and shirts or jockets, thereby acting as a barrier to fluid transport. In addition however, the breathable backsheet of the present invention permits the transfer of at least water vapour, preferably both water vapour and air through it and thus allows the circulation of air into and water vapour out of the article. The backsheet typically extends across the whole of the absorbent structure and can extend into and form part or all of sideflaps, side wrapping elements or wings, if present.

According to the present invention a dual or multiple layer breathable backsheet composite is used in the absorbent article. According to the present invention suitable breathable backsheets for use herein comprise at least a first and a second layer with said first layer being an air permeable layer. Preferred breathable backsheets for use herein are those having a high vapour exchange, most preferably both a high vapour and high air exchange.

The first layer is indicated as layer 50 in the drawings. It is positioned between the garment facing surface of the absorbent core and the wearer facing surface of the second layer which is indicated as layer 52 in FIG. 1. It is oriented such that it retards or prevents liquid from passing from the absorbent core towards the outside while allowing free air flow through it.

According to the present invention the second layer (52) needs to provide at least water vapour permeability so as to support breathability of the article. It is not required but desirable that it also supports air permeability in order to further improve the comfort benefit from the breathability of the article. In this context suitable water vapour and air permeable layers include two-dimensional micro- or macro-apertured films, which can also be micro- or macroscopically expended films, formed apertured films and monolithic films, as well as nonwovens, or wovens.

Suitable 2 dimensional planar layers of the backsheet may be made of any material known in the art, but are preferably manufactured from commonly available polymeric materials. Suitable materials are for example Goretex (TM) or Sympatex (TM) type materials well known in the art for their application in so-called breathable clothing. Other suitable materials include XMP-1001 of Minnesota Mining and Manufacturing Company, St. Paul, Minn., USA and Exxaire XBF-101W, supplied by the Exxon Chemical Company. As used herein the term 2 dimensional planar layer refers to layers having a depth of less than 1 mm, preferably less than 0.5 mm, wherein the apertures do not protrude out of the plane of the layer. The apertured materials for use as a backsheet in the present invention may be produced using any of the methods known in the art such as described in EPO 293 482 and the references therein. In addition the dimensions of the apertures produced by this method may be increased by applying a force across the plane of the backsheet layer (i.e. stretching the layer).

Suitable apertured formed films include films which have discrete apertures which extend beyond the horizontal plane of the garment facing surface of the layer towards the core thereby forming protuberances. The protuberances have an orifice located at its terminating end. Preferably said protuberances are of a funnel shape, similar to those described in U.S. Pat. No. 3,929,135. The apertures located within the plane and the orifices located at the terminating end of protuberance themselves maybe circular or non circular provided the cross sectional dimension or area of the orifice at the termination of the protuberance is smaller than the cross sectional dimension or area of the aperture located within the garment facing surface of the layer. Preferably said apertured preformed films have a directional liquid transport and are positioned such that they support the prevention of liquid loss (leakage) through the backsheet. Suitable macroscopically expanded films for use herein include films as described for example in U.S. Pat. Nos. 4,637,819 and 4,591,523.

Suitable monolithic films include Hytrel™, available from DuPont Corporation, USA, and other such materials as described in Index 93 Congress, Session 7A "Adding value to Nonwovens", J-C. Cardinal and Y. Trouilhet, DuPont de Nemours international S.A, Switzerland. Suitable non-wovens and/or wovens are any of those well known in the art. Non-wovens such as spunbonded, melt blown or carded which are thermobonded airlayed, drylayed or even wet-layed with or without binder can be used. Particularly preferred non-wovens are multilayer non-wovens such as a composite of fine melt blown fibers with more coarse spunbonded fibers with the meltblown fibers forming the wearer facing surface of the non-woven layer.

The first layer according to the present invention is preferably in direct contact with the absorbent core. It provides air and water vapour permeability by being apertured. Preferably this layer is made in accordance with the aforementioned U.S. Pat. No. 5,591,510 or PCT WO-97/03818, WO-97/03795. In particular, this layer comprises a polymeric film indicated in FIG. 1 as first layer (50), having capillaries (54). The capillaries extend away from the wearer facing surface of film (50) at an angle which is less then 90 degrees. In FIGS. 2 through 7 alternative embodiments of such capillaries are shown. Preferably the capillaries are evenly distributed across the entire surface of the layer, and are all identical. However, layers having only certain regions of the surface provided with apertures, for example only an area outside the region aligned with the central loading zone of the absorbent core, maybe provided with capillaries according to the present invention.

Methods for making such three-dimensional polymeric films with capillary apertures are identical or similar to those found in the apertured film topsheet references, the apertured formed film references and the micro-/macroscopically expended film references cited above. Typically a polymeric film such as a polyethylene (LDPE, LLDPE, MDPE, HDPE or laminates thereof) is heated close to its melting point and exposed through a forming screen to a suction force which pulls those areas exposed to the force into the forming apertures which are shaped such that the film is formed into that shape and, when the suction force is high enough, the film breaks at its end thereby forming an aperture through the film.

Various forms, shapes, sizes and configurations of the capillaries are possible and will be discussed in reference to FIGS. 2 through 7 in the following. The apertures (53) form capillaries (54) which have side walls (56). The capillaries extend away from the wearer facing surface of the film (55) for a length which typically should be at least in the order of magnitude of the largest diameter of the aperture while this distance can reach up to several times the largest aperture diameter. The capillaries have a first opening (57) in the plane of the garment facing surface of the film (55) and a second opening (58) which is the opening formed when the suction force (such as a vacuum) in the above mentioned process creates the aperture. Naturally the edge of the second opening (58) may be rugged or uneven, comprising loose elements extending from the edge of the opening. However, it is preferred that the opening be as smooth as possible so as not to create a liquid transport entanglement between the extending elements at the end of the second opening (58) of the capillary (54) with the absorbent core (44) in the absorbent article (in contrast this may be desirable for apertured film topsheets where such loose elements provide the function of sucker feet).

Figure 4:
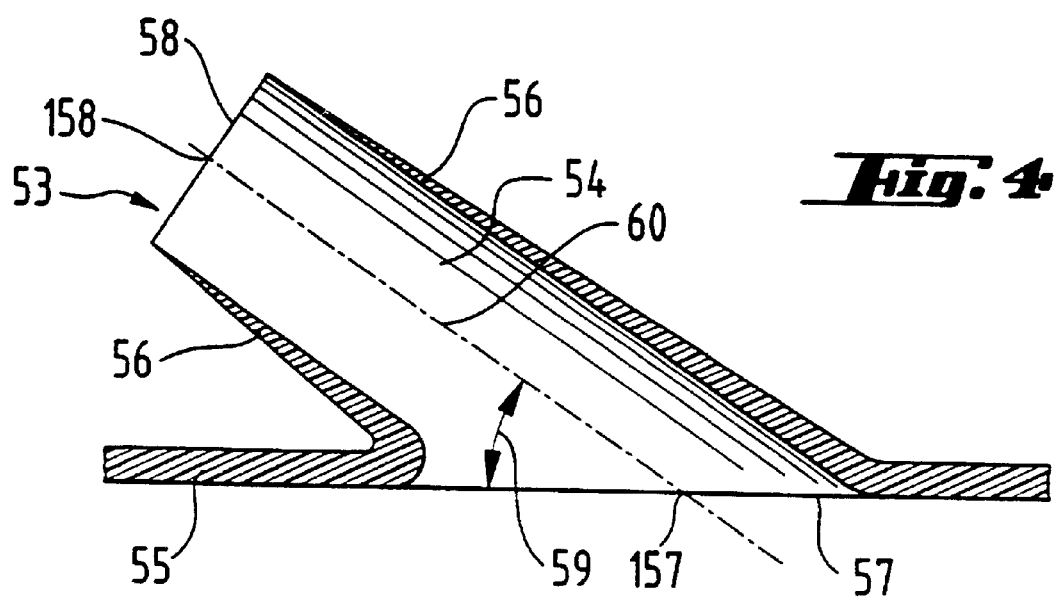

As shown in FIG. 4 the first opening has a center point (157) and the second opening also has a center point (158). These center points for non-circular openings are the area center points of the respective opening area. When connecting the center point (157) of the first opening (57) with the center point (158) of the second opening (58) a center axis (60) is defined. This center axis (60) forms an angle (59) with the plain of the film which is the same plain as the garment facing surface of the film (55). This angle should be preferably in the range between 85 and 20 degrees, more preferably between 65 degrees and 25 degrees, and most preferably between 55 and 30 degrees.

Figure 2:
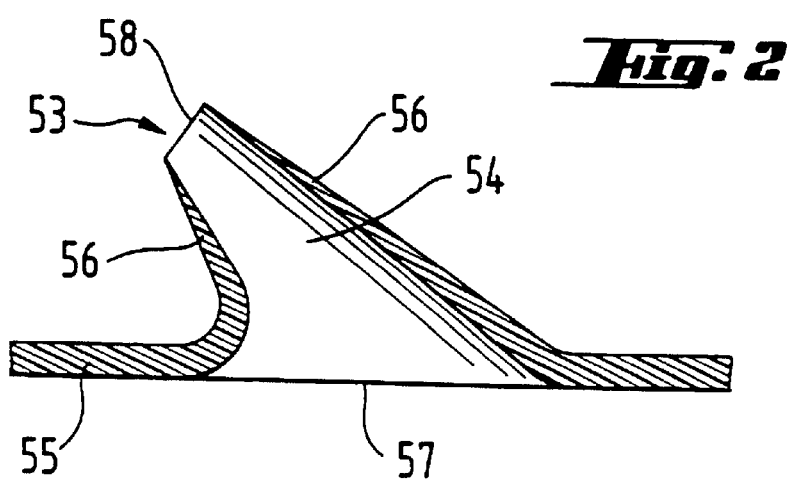
Figure 3:
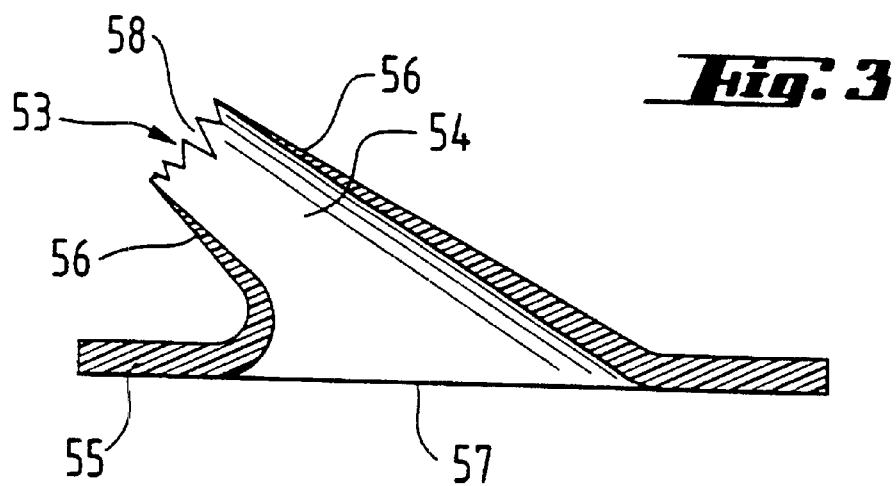

It is of course possible to allow the capillaries to take the shape of a funnel such that the second opening (58) is (substantially) smaller than the first opening (57) when considering the opening size in a plain perpendicular to the center axis (60). Such an embodiment is shown in FIG. 3 and FIG. 2. In FIG. 2 it is also shown that the wall (56) of the capillary may not end in the second opening (58) such that the opening forms a surface perpendicular to the center axis (60) but such that the wall on the portion of the capillary further apart from the wearer facing surface of the film (55) extends over the opening to further aid the film in reducing the probability of liquid migrating through the capillaries from the absorbent core on the wearer facing side of the film (55) to the garment facing side of the film (and cause leakage).

In FIG. 5 another embodiment of the capillaries useful for the present invention is shown which is curved along its length towards the wearer facing surface of the film (55). This has a similar effect as the extension of the wall (56) as shown in FIG. 2.

Figure 7:
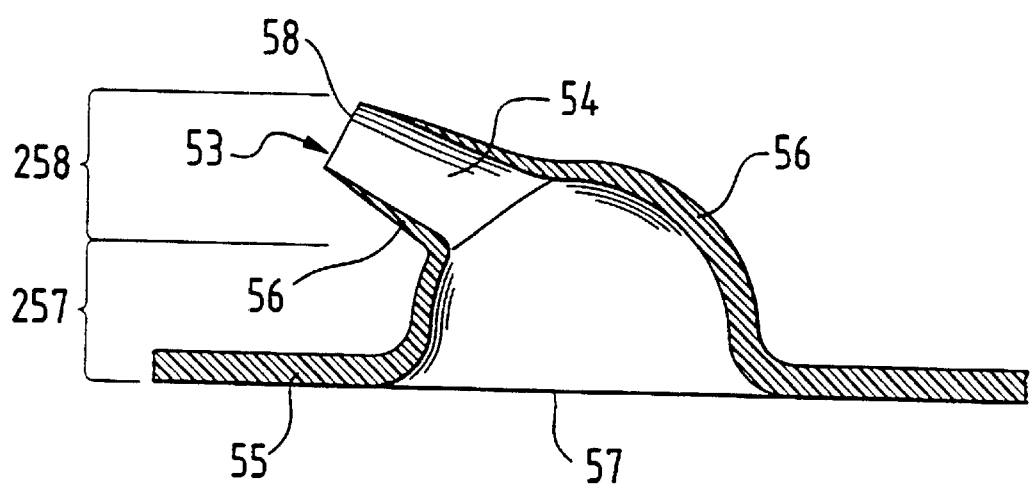

In FIG. 6 another preferred embodiment of a capillary according to the present invention is shown which has a first portion (257) and a second portion (258). The first portion (257) of the capillary is different in direction than the second portion (258) of the capillary (54). This difference can also be in shape, size, and form of the portions of the capillary in order to achieve the desired level of breathability while preventing liquid passage through the film in a direction from the wearer facing side towards the garment facing side. Such an example is shown in FIG. 7.

Without wishing to be bound by theory it is believed that the capillaries according to the present invention in the first layer of the breathable backsheet allow air and water vapour permeability which is not hindered by them being slanted at an angle or by the shape as indicated above. At the same time the slanting and shaping according to the present invention will allow the capillaries to close under pressure excerpted from the wearer facing side on them such that liquid transport through the capillaries towards the outside of the article becomes nearly impossible. Hence these three-dimensional formed film layers are highly preferable in the context of breathable absorbent articles and in particular so if an additional second outer layer is provided.

Absorbent Article Construction

A further aspect of the present invention relates to the joining of the topsheet, backsheet and absorbent core elements to provide the absorbent article. According to the present invention at least two, preferably all of the elements of the article are joined.

Each of said elements comprising at least one layer has a wearer facing surface and a garment facing surface. Typically, adjacent garment facing surfaces form a common interface with the wearer facing surface of an adjacent element or layer. The elements or layers are joined together across this common interface. In this manner the topsheet is joined to the absorbent core, and the core is joined to the backsheet. Furthermore, each of said topsheet, backsheet and core elements may comprise more than one layer and these layers may also be similarly joined. In addition the topsheet may be directly or indirectly joined to the backsheet at the periphery of the absorbent article to contain the absorbent core.

The elements and layers thereof may be joined by any means known in the art for affixing two adjacent layers of material, such that the layers are directly attached to one another or directly attached to one another via the joining means. Suitable joining means include adhesive, fusion bonding, ultra sonic bonding, stitching, heat (e.g. thermo-bonding by welding fibers at intersections or melting a polymer to attach fibers or films to each other), embossing, crimping, pressure bonds, dynamic mechanical bonds or combinations thereof. According to an embodiment of the present invention the preferred means of joining is adhesive. Suitable adhesives include non pressure sensitive and cold adhesives. The adhesive may be applied by any means known in the art such as spiral application, slot coating, spraying, spiral spraying, curtain coating, contact coating and printing, provided that the adhesive does not substantially affect the breathability and other functions of the elements of the article.

One means of achieving this is to use particular adhesive application methods such as open adhesive application techniques, whereby areas of the common interface are adhesive free, whilst retaining the required level of attachment/joining of the two adjacent layers or elements. In particular spiral spraying is preferred.

In a preferred embodiment of the present invention wherein the absorbent article finds utility as a sanitary napkin or panty liner, the absorbent article is also provided with a panty fastening means which provides means to attach the article to an undergarment. For example the panty fastening means may comprise a mechanical fastener such as hook and loop fasteners such as marketed under the tradename VELCRO, snaps or holders. Alternatively, the article is fastened to the undergarment by means of panty fastening adhesive on the backsheet. The panty fastening adhesive provides a means for securing the article to the panty and preferably a means for securing the article when soiled, to the fold and wrap package for convenient disposal. Typically, at least a portion of the garment facing surface of the backsheet is coated with adhesive to form the panty fastening adhesive. Any adhesive or glue used in the art for such purposes can be used for the panty fastening adhesive herein. Pressure sensitive adhesives are most preferred. Suitable adhesives include Century A-305-IV manufactured by the Century Adhesives Corporation of Columbus, Ohio, and Instant LOK 34-2823 manufactured by the National Starch and Chemical Company of Bridgewater, New Jersey, 3 Sigma 3153 manufactured by 3 Sigma and Fuller H-2238ZP manufactured by the H.B. Fuller Co.

In order to reduce the adverse effect on breathablility of the backsheet (and thus of the article as a whole), the adhesive is preferably applied such that at least 60%, preferably from at least 80%, most preferably at least 90% of the surface of the backsheet is adhesive free. The required adhesiveness can still be achieved even when using reduced surface coverage by using a particular distribution such as thinner strips, discontinuous strips of adhesive, intermittant dots, random patterns or spirals.

The panty fastening adhesive is typically covered with a removable release paper or film in order to prevent the adhesive from drying out or adhering to another surface other than the panty prior to use. Any commercially available release paper or film may be used. Suitable examples include BL 30MG-A SILOX EI/O and BL 30 MG-A SILOX 4 P/O available from Akrosil Corporation.

According to the present invention the absorbent article can be used beneficially in the context of sanitary napkins, panty liners, incontinence articles, sweatpads and diapers. However, sanitary napkins are particularly susceptible to the present invention. The disposable article may thus also have all those features and parts which are typical for products in the context of their intended use.

What is claimed is:

1. Breathable disposable absorbent article of layered construction, each layer or system of layers having a garment facing surface, which is oriented to face in a direction of a garment (21) during use of the article, and a wearer facing surface, which is oriented to face in the direction of the wearer (20) during use of the article, said article comprising at least an absorbent core (40, 42, 44);

a breathable backsheet (50, 52) located on said garment facing surface of said absorbent core (40, 42, 44), said backsheet (50, 52) comprising at least a first backsheet layer (50) and a second backsheet layer (52), said first backsheet layer (50) being positioned between said garment facing surface of said absorbent core (40, 42, 44) and said wearer facing surface of said second backsheet layer (52), said first and said second backsheet layers (50, 52) being water vapor permeable, said first backsheet layer (50) comprising a resilient, three dimensional web, said web consists of a liquid impervious polymeric film (55) having apertures (53), said apertures (53) forming capillaries (54), said capillaries (54) having side walls (56) which extend away from said wearer facing surface of said film (55), said capillaries (54) having a first opening (57) in said garment facing surface of said film (55) and a second opening (58) at the end of said capillaries (54) spaced apart from said wearer facing surface of said film (55)

said article being characterised in that said capillaries (54) extend away from said wearer facing surface of said film (55) at an angle (59) of less than 90° measured from the plain of said film.

2. Breathable disposable article according to claim 1 wherein that said wearer facing surface of said web is the wearer facing surface of said backsheet.

3. Breathable disposable article according to claim 1 wherein that said capillaries are all substantially identical.

4. Breathable disposable article according to claim 1 wherein that said capillaries are homogeneously distributed across said film.

5. Breathable disposable article according to claim 1 wherein that said first opening of each of said capillaries has a center point and said second opening of each of said capillaries also has a center point and a line connecting said center points defines a center axis of each of said capillaries, said center axis forming an angle with the plane of said film, said angle being between 85° and 20°.

6. Breathable disposable article according to claim 5 wherein that said angle is between 65° and 25°.

7. Breathable disposable article according to claim 6 wherein that said angle is between 55° and 30°.

8. Breathable disposable article according to claim 1 wherein that at least some of said capillaries form cones having liquid transport areas which are reducing in a direction towards the absorbent core when comparing areas perpendicular to said center axis.

9. Breathable disposable article according to claim 1 wherein that said capillaries are curved towards said plane of said film.

10. Breathable disposable article according to claim 1 wherein that said capillaries have a first portion being different in direction, form, shape, size or combinations thereof than said second portion.

11. Breathable disposable article according to claim 1 wherein that said second opening at least of some of said capillaries have generally the form of a slit having a length which is at least 5 times as large as the width of said slit.

* * * * *